United States Patent
Van Ginckel et al.

(10) Patent No.: US 6,545,020 B1
(45) Date of Patent: Apr. 8, 2003

(54) FARNESYL PROTEIN TRANSFERASE INHIBITORS WITH IN VIVO RADIOSENSITIZING PROPERTIES

(75) Inventors: Robert Franciscus Van Ginckel, Vorselaar (BE); Wim Joanna Floren, Rijkevorsel (BE); David William End, Ambler, PA (US); Walter Boudewijin Leopold Wouters, Kapellen (BE)

(73) Assignee: Janssen Pharmaceutica, N.V. (BE)

( * ) Notice: Subject to any disclaimer, the term of this patent is extended or adjusted under 35 U.S.C. 154(b) by 0 days.

(21) Appl. No.: 09/743,130

(22) PCT Filed: Jun. 30, 1999

(86) PCT No.: PCT/EP99/04545

§ 371 (c)(1),
(2), (4) Date: Jan. 3, 2001

(87) PCT Pub. No.: WO00/01411

PCT Pub. Date: Jan. 13, 2000

(30) Foreign Application Priority Data

Jul. 6, 1998 (EP) ............................................. 98202257
Dec. 18, 1998 (EP) ............................................. 98204330

(51) Int. Cl.[7] .............................................. A61K 31/47
(52) U.S. Cl. ........................ 514/312; 514/311; 514/314
(58) Field of Search ................................ 514/311, 312, 514/314

(56) References Cited

U.S. PATENT DOCUMENTS 5,602,184 A     2/1997  Myers et al.
6,258,824 B1 *  7/2001  Yang .......................... 514/312

FOREIGN PATENT DOCUMENTS

| WO | WO 00/01411 | 1/1997 |
| WO | WO 97/16443 | 5/1997 |
| WO | WO 97/21701 | 6/1997 |
| WO | WO 97/38697 | 10/1997 |
| WO | WO 98/40383 | 9/1998 |

OTHER PUBLICATIONS

Bernhard et al., Cancer Research, vol. 56, Apr. 15, 1996, "The Farnesyltransferase Inhibitor FTI–277 Radiosensitizes H–ras–transformed Rat Embryo Fibroblasts,"pp. 1727–1730.

Rak et al., Cancer Research, vol. 55, Oct. 15, 1995, "Mutant ras Oncogenes Upregulate VEGF/VPF Expression: Implications for Induction and Inhibition of Tumor Angiogenesis," pp. 4575–4580.

* cited by examiner

*Primary Examiner*—James H. Reamer
(74) *Attorney, Agent, or Firm*—Myra McCormack; Alana G Kriegsman

(57) ABSTRACT

The present invention is concerned with the finding that farnesyl protein transferase inhibitors have radiosensitizing properties which makes them useful for preparing a pharmaceutical composition for administration before, during or after irradiation of a tumor for treating cancer in vivo.

15 Claims, No Drawings

FARNESYL PROTEIN TRANSFERASE INHIBITORS WITH IN VIVO RADIOSENSITIZING PROPERTIES

CROSS REFERENCE TO RELATED APPLICATIONS

This application is the National Stage application under 35 U.S.C. §371 of International Application No. PCT/EP99/04545 filed Jun. 30, 1999, which claims priority from EP 98202257.6, filed Jul. 6, 1998, and EP 98204330.9, filed Dec. 18, 1998, the contents of all of which are hereby incorporated by reference.

The present invention is concerned with the finding that farnesyl protein transferase inhibitors have radiosensitizing properties which makes them useful for preparing a pharmaceutical composition for administration before, during or after irradiation of a tumor for treating cancer in vivo.

WO-97/21701 describes the preparation, formulation and pharmaceutical properties of farnesyl protein transferase inhibiting (imidazoly-5-yl)methyl-2-quinolinone derivatives of formulas (I), (II) and (III), as well as intermediates of formula (II) and (III) that are metabolized in vivo to the compounds of formula (I). The compounds of formulas (I), (II) and (III) are represented by

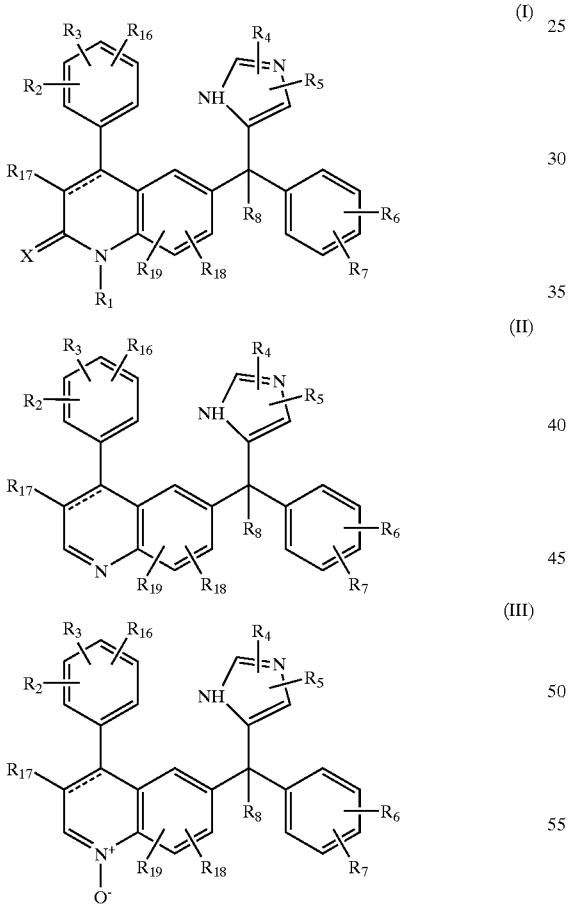

the pharmaceutically acceptable acid or base addition salts and the stereochemically isomeric forms thereof, wherein
the dotted line represents an optional bond;
X is oxygen or sulfur;
$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —$Alk^1$—C(=O)—$R^9$, —$Alk^1$—S(O)—$R^9$ or —$Alk^1$—S(O)$_2$—$R^9$, wherein $Alk^1$ is $C_{1-6}$alkanediyl,
$R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;
$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or
when on adjacent positions $R^2$ and $R^3$ taken together may form a bivalent radical of formula

| | |
|---|---|
| —O—CH$_2$—O— | (a-1), |
| —O—CH$_2$—CH$_2$—O— | (a-2), |
| —O—CH=CH— | (a-3), |
| —O—CH$_2$—CH$_2$— | (a-4), |
| —O—CH$_2$—CH$_2$—CH$_2$— | (a-S), or |
| —CH=CH—CH=CH— | (a-6); |

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;
$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or
when on adjacent positions $R^6$ and $R^7$ taken together may form a bivalent radical of formula

| | |
|---|---|
| —O—CH$_2$—O— | (c-1), or |
| —CH=CH—CH=CH— | (c-2); |

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula

| | |
|---|---|
| —O—$R^{10}$ | (b-1), |
| —S—$R^{10}$ | (b-2), |
| —N—$R^{11}R^{12}$ | (b-3), | wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, or a radical or formula —$Alk^2$—OR$^{13}$ or —$Alk^2$—NR$^{14}R^{15}$;
$R^{11}$ is hydrogen, $C_{1-12}$alkyl, $Ar^1$ or $Ar^2C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl$C_{1-6}$alkyl, a natural amino acid, $Ar^1$carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk$^2$—OR$^{13}$ or —Alk$^2$—NR$^{14}$R$^{15}$;

wherein Alk$^2$ is $C_{1-6}$alkanediyl;

R$^{13}$ is hydrogen, $C_{1-6}$alkyl, $C_{1-6}$alkylcarbonyl, hydroxy$C_{1-6}$alkyl, Ar$^1$ or Ar$^2$$C_{1-6}$alkyl;

R$^{14}$ is hydrogen, $C_{1-6}$alkyl, Ar$^1$ or Ar$^2$$C_{1-6}$alkyl;

R$^{15}$ is hydrogen, $C_{1-6}$alkyl, $C_{1-6}$alkylcarbonyl, Ar$^1$ or Ar$^2$$C_{1-6}$alkyl;

R$^{17}$ is hydrogen, halo, cyano, $C_{1-6}$alkyl, $C_{1-6}$alkyloxycarbonyl, Ar$^1$;

R$^{18}$ is hydrogen, $C_{1-6}$alkyl, $C_{1-6}$alkyloxy or halo;

R$^{19}$ is hydrogen or $C_{1-6}$alkyl;

Ar$^1$ is phenyl or phenyl substituted with $C_{1-6}$alkyl, hydroxy, amino, $C_{1-6}$alkyloxy or halo; and Ar$^2$ is phenyl or phenyl substituted with $C_{1-6}$alkyl, hydroxy, amino, $C_{1-6}$alkyloxy or halo.

WO-97/16443 concerns the preparation, formulation and pharmaceutical properties of farnesyl protein transferase inhibiting compounds of formula (IV), as well as intermediates of formula (V) and (VI) that are metabolized in vivo to the compounds of formula (IV). The compounds of formulas (IV), (V) and (VI) are represented by

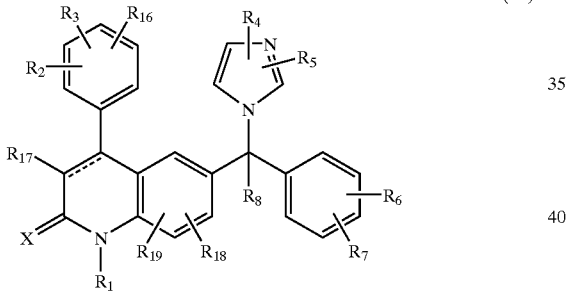

(IV)

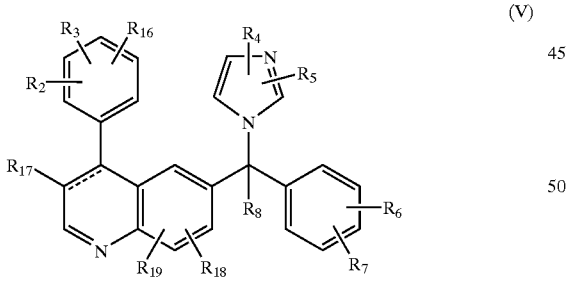

(V)

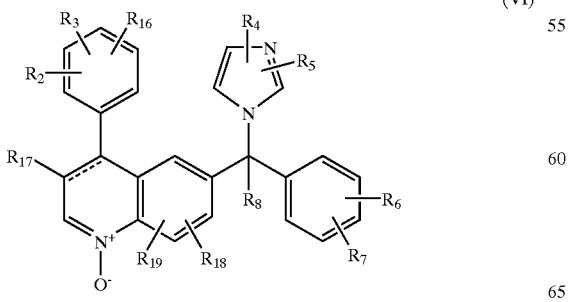

(VI)

the pharmaceutically acceptable acid or base addition salts and the stereochemically isomeric forms thereof, wherein the dotted line represents an optional bond;

X is oxygen or sulfur;

R$^1$ is hydrogen, $C_{1-12}$alkyl, Ar$^1$, Ar$^2$$C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —Alk$^1$—C(=O)—R$^9$, —Alk$^1$—S(O)—R$^9$ or —Alk$^1$—S(O)$_2$—R$^9$, wherein Alk$^1$ is $C_{1-6}$alkanediyl, R$^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

R$^2$ and R$^3$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, Ar$^1$, Ar$^2$$C_{1-6}$alkyl, Ar$^2$oxy, Ar$^2$$C_{1-6}$alkyloxy, hydroxycarbonyl, $C_{1-6}$alkyloxycarbonyl, trihalomethyl, trihalomethoxy, $C_{2-6}$alkenyl; or when on adjacent positions R$^2$ and R$^3$ taken together may form a bivalent radical of formula —O—CH$_2$—O— (a-1), —O—CH$_2$—CH$_2$—O— (a-2), —O—CH=CH— (a-3), —O—CH$_2$—CH$_2$— (a-4), —O—CH$_2$—CH$_2$—CH$_2$— (a-5), or —CH=CH—CH=CH— (a-6);

R$^4$ and R$^5$ each independently are hydrogen, Ar$^1$, $C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2$$C_{1-6}$alkyl;

R$^6$ and R$^7$ each independently are hydrogen, halo, cyano, $C_{1-6}$alkyl, $C_{1-6}$alkyloxy or Ar$^2$oxy;

R$^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, hydroxycarbonyl$C_{1-6}$alkyl, hydroxy$C_{1-6}$alkyl, amino$C_{1-6}$alkyl, mono- or di($C_{1-6}$alkyl)amino$C_{1-6}$alkyl, halo$C_{1-6}$alkyl, $C_{1-6}$alkyloxy$C_{1-6}$alkyl, aminocarbonyl$C_{1-6}$alkyl, Ar$^1$, Ar$^2$$C_{1-6}$alkyloxy$C_{1-6}$alkyl, $C_{1-6}$alkylthio$C_{1-6}$alkyl;

R$^{10}$ is hydrogen, $C_{1-6}$alkyl, $C_{1-6}$alkyloxy or halo;

R$^{11}$ is hydrogen or $C_{1-6}$alkyl;

Ar$^1$ is phenyl or phenyl substituted with $C_{1-6}$alkyl, hydroxy, amino, $C_{1-6}$alkyloxy or halo;

Ar$^2$ is phenyl or phenyl substituted with $C_{1-6}$alkyl, hydroxy, amino, $C_{1-6}$alkyloxy or halo.

PCT/EP98/01296, filed Mar. 3, 1998, concerns the preparation, formulation and pharmaceutical properties of farnesyl protein transferase inhibiting compounds of formula (VII)

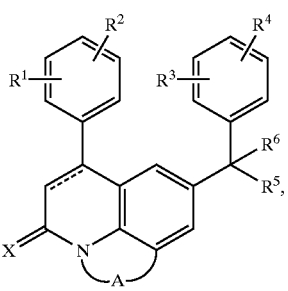

(VII)

the pharmaceutically acceptable acid addition salts and the stereochemically isomeric forms thereof, wherein the dotted line represents an optional bond;
X is oxygen or sulfur;
—A— is a bivalent radical of formula

| —CH=CH— | (a-1), |
| —CH$_2$—CH$_2$— | (a-2), |
| —CH$_2$—CH$_2$—CH$_2$— | (a-3), |
| —CH$_2$—O— | (a-4), |
| —CH$_2$—CH$_2$—O— | (a-5), |
| —CH$_2$—S— | (a-6), |
| —CH$_2$—CH$_2$—S— | (a-7), |
| —CH=N— | (a-8), |
| —N=N— | (a-9), or |
| —CO—NH— | (a-10); | wherein optionally one hydrogen atom may be replaced by $C_{1-4}$alkyl or $Ar^1$;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^2$, $Ar^2$—$C_{1-6}$alkyl, $Ar^2$-oxy, $Ar^2$—$C_{1-6}$alkyloxy;

or when on adjacent positions $R^1$ and $R^2$ taken together may form a bivalent radical of formula

| —O—CH$_2$—O— | (b-1), |
| —O—CH$_2$—CH$_2$—O— | (b-2), |
| —O—CH=CH— | (b-3), |
| —O—CH$_2$—CH$_2$— | (b-4), |
| —O—CH$_2$—CH$_2$—CH$_2$— | (b-5), or |
| —CH=CH—CH=CH— | (b-6); |

$R^3$ and $R^4$ each independently are hydrogen, halo, cyano, $C_{1-6}$alkyl, $C_{1-6}$alkyloxy, $Ar^3$-oxy, $C_{1-6}$alkylthio, di($C_{1-6}$alkyl)amino, trihalomethyl, trihalomethoxy, or when on adjacent positions $R^3$ and $R^4$ taken together may form a bivalent radical of formula

| —O—CH$_2$—O— | (C-1), |
| —O—CH$_2$—CH$_2$—O— | (c-2), or |
| —CH=CH—CH=CH— | (c-3); |

$R^5$ is a radical of formula

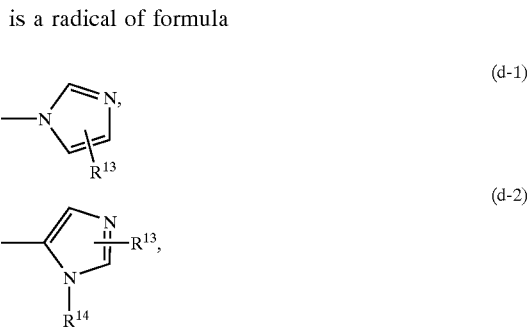

wherein $R^{13}$ is hydrogen, halo, $Ar^4$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, $C_{1-6}$alkyloxycarbonyl, $C_{1-6}$alkylS(O)$C_{1-6}$alkyl or $C_{1-6}$alkylS(O)$_2$$C_{1-6}$alkyl;

$R^{14}$ is hydrogen, $C_{1-6}$alkyl or di($C_{1-4}$alkyl) aminosulfonyl;

$R^6$ is hydrogen, hydroxy, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl$C_{1-6}$alkyl, $C_{1-6}$alkyloxycarbonyl, mono- or di($C_{1-6}$alkyl) amino$C_{1-6}$alkyl, $Ar^5$, $Ar^5$—$C_{1-6}$alkyloxy$C_{1-6}$alkyl; or a radical of formula

| —O—$R^7$ | (e-1), |
| —S—$R^7$ | (e-2), |
| —N—$R^8R^9$ | (e-3), | wherein $R^7$ is hydrogen, $C_{1-6}$alkyl, $C_{1-6}$alkylcarbonyl, $Ar^6$, $Ar^6$—$C_{1-6}$alkyl, $C_{1-6}$alkyloxycarbonyl$C_{1-6}$alkyl, or a radical of formula —Alk—$OR^{10}$ or —Alk—$NR^{11}R^{12}$;

$R^8$ is hydrogen, $C_{1-6}$alkyl, $Ar^7$ or $Ar^7$—$C_{1-6}$alkyl;

$R^9$ is hydrogen, $C_{1-6}$alkyl, $C_{1-6}$alkylcarbonyl, $C_{1-6}$alkyloxycarbonyl, $C_{1-6}$alkylaminocarbonyl, $Ar^8$, $Ar^8$—$C_{1-6}$alkyl, $C_{1-6}$alkylcarbonyl$C_{1-6}$alkyl, $Ar^8$-carbonyl, $Ar^8$—$C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—$OR^{10}$ or —Alk—$NR^{11}R^{12}$;

wherein Alk is $C_{1-6}$alkanediyl;

$R^{11}$ is hydrogen, $C_{1-6}$alkyl, $C_{1-6}$alkylcarbonyl, hydroxy$C_{1-6}$alkyl, $Ar^9$ or $Ar^9$—$C_{1-6}$alkyl;

$R^{11}$ is hydrogen, $C_{1-6}$alkyl, $C_{1-6}$alkylcarbonyl, $Ar^{10}$ or $Ar^{10}$—$C_{1-6}$alkyl;

$R^{12}$ is hydrogen, $C_{1-6}$alkyl, $Ar^{11}$ or $Ar^{11}$—$C_{1-6}$alkyl; and $Ar^1$ to $Ar^{11}$ are each independently selected from phenyl; or phenyl substituted with halo, $C_{1-6}$alkyl, $C_{1-6}$alkyloxy or trifluoromethyl.

PCT/EP98/02357, filed Apr. 17, 1998, concerns the preparation, formulation and pharmaceutical properties of farnesyl protein transferase inhibiting compounds of formula (VIII)

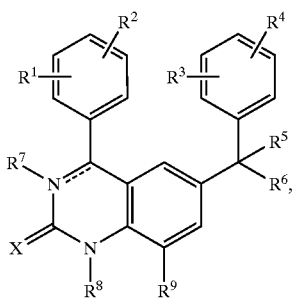

(VIII)

the pharmaceutically acceptable acid addition salts and the stereochemically isomeric forms thereof, wherein the dotted line represents an optional bond;

X is oxygen or sulfur;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^1$, $Ar^1C_{1-6}$alkyl, $Ar^1$oxy or $Ar^1C_{1-6}$ alkyloxy;

$R^3$ and $R^4$ each independently are hydrogen, halo, cyano, $C_{1-6}$alkyl, $C_{1-6}$alkyloxy, $Ar^1$oxy, $C_{1-6}$alkylthio, di($C_{1-6}$alkyl)amino, trihalomethyl or trihalomethoxy;

$R^5$ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl$C_{1-6}$alkyl, $C_{1-6}$alkyloxycarbonyl, mono- or di($C_{1-6}$alkyl)amino$C_{1-6}$ alkyl, $Ar^1$, $Ar^1C_{1-6}$alkyloxy$C_{1-6}$alkyl; or a radical of formula —O—$R^{10}$      (a-1), —S—$R^{10}$      (a-2), —N—$R^{11}R^{12}$      (a-3), wherein $R^{10}$ is hydrogen, $C_{1-6}$alkyl, $C_{1-6}$alkylcarbonyl, $Ar^1$, $Ar^1C_{1-6}$alkyl, $C_{1-6}$alkyloxycarbonyl$C_{1-6}$alkyl, or a radical of formula —Alk—$OR^{13}$ or —Alk—$NR^{14}R^{15}$;

$R^{11}$ is hydrogen, $C_{1-6}$alkyl, $Ar^1$ or $Ar^1C_{1-6}$alkyl;

$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^1C_{1-6}$alkyl, $C_{1-6}$alkylcarbonyl$C_{1-6}$alkyl, $Ar^1$carbonyl, $Ar^1C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—$OR^{13}$ or —Alk—$NR^{14}R^{15}$;

wherein Alk is $C_{1-6}$alkanediyl;

$R^{13}$ is hydrogen, $C_{1-6}$alkyl, $C_{1-6}$alkylcarbonyl, hydroxy$C_{1-6}$alkyl, $Ar^1$ or $Ar^1C_{1-6}$alkyl;

$R^{14}$ is hydrogen, $C_{1-6}$alkyl, $Ar^1$ or $Ar^1C_{1-6}$alkyl;

$R^{15}$ is hydrogen, $C_{1-6}$alkyl, $C_{1-6}$alkylcarbonyl, $Ar^1$ or $Ar^1C_{1-6}$alkyl;

$R^6$ is a radical of formula

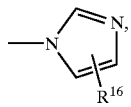 (b-1)

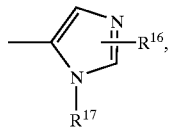 (b-2)

wherein $R^{16}$ is hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2C_{1-6}$alkyl;

$R^{17}$ is hydrogen, $C_{1-6}$alkyl or di($C_{1-4}$alkyl) aminosulfonyl;

$R^7$ is hydrogen or $C_{1-6}$alkyl provided that the dotted line does not represent a bond;

$R^8$ is hydrogen, $C_{1-6}$alkyl or $Ar^2CH_2$ or $Het^1CH_2$;

$R^9$ is hydrogen, $C_{1-6}$alkyl, $C_{1-6}$alkyloxy or halo; or $R^8$ and $R^9$ taken together to form a bivalent radical of formula —CH=CH—      (c-1), —CH$_2$—CH$_2$—      (c-2), —CH$_2$—CH$_2$—CH$_2$—      (c-3), —CH$_2$—O—      (c-4), or —CH$_2$—CH$_2$—O—      (c-5);

$Ar^1$ is phenyl; or phenyl substituted with 1 or 2 substituents each independently selected from halo, $C_{1-6}$alkyl, $C_{1-6}$alkyloxy or trifluoromethyl;

$Ar^2$ is phenyl; or phenyl substituted with 1 or 2 substituents each independently selected from halo, $C_{1-6}$alkyl, $C_{1-6}$alkyloxy or trifluoromethyl; and $Het^1$ is pyridinyl; pyridinyl substituted with 1 or 2 substituents each independently selected from halo, $C_{1-6}$alkyl, $C_{1-6}$alkyloxy or trifluoromethyl.

Other useful farnesyl protein transferase inhibitors have the structure

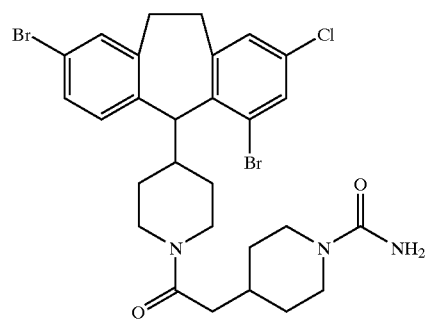

SCH-66336

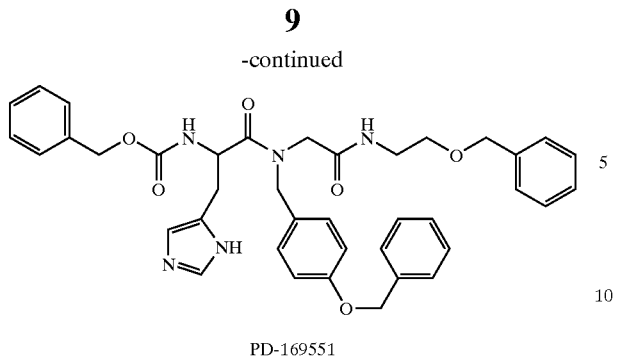

PD-169551

These farnesyl protein transferase inhibitors decrease the growth of tumors in vivo by a direct effect on tumor cell growth but also indirectly, i.e. by inhibiting angiogenesis (Rak. J. et al, Cancer Research, 55, 4575–4580, 1995). Consequently, treatment with these inhibitors suppresses solid tumor growth in vivo at least in part by inhibiting angiogenesis. This being the case, one could expect that treatment with these compounds could result in hypoxic tumors, thereby inducing or causing increased radio-resistance.

Unexpectedly, we have now found that that does not happen. On the contrary, it appears that administration of a farnesyl protein transferase inhibitor as described hereinbefore sensitizes tumor cells in vivo to irradiation or ionizing radiation and moreover, resensitizes radioresistant cells. Thus, farnesyl protein transferase inhibitors are useful as in vivo radiosensitizing (radiation-sensitizing or radiation-potentiating) agents.

The present invention is concerned with the use of at least a farnesyl protein transferase inhibitor for the preparation of a pharmaceutical composition having radiosensitizing properties for administration before, during or after irradiation of a tumor for treating cancer in vivo.

In particular, the present invention is concerned with the use of at least a farnesyl protein transferase inhibitor for the preparation of a pharmaceutical composition having radiosensitizing properties for administration before, during or after irradiation of a tumor for treating cancer in vivo, wherein said farnesyl protein transferase inhibitor is an (imidazoly-5-yl)methyl-2-quinolinone derivative of formula (I), or a compound of formula (II) or (III) which is metabolized in vivo to the compound of formula (I), said compounds being represented by

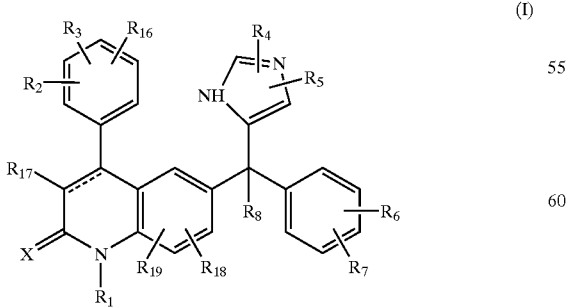 (I)

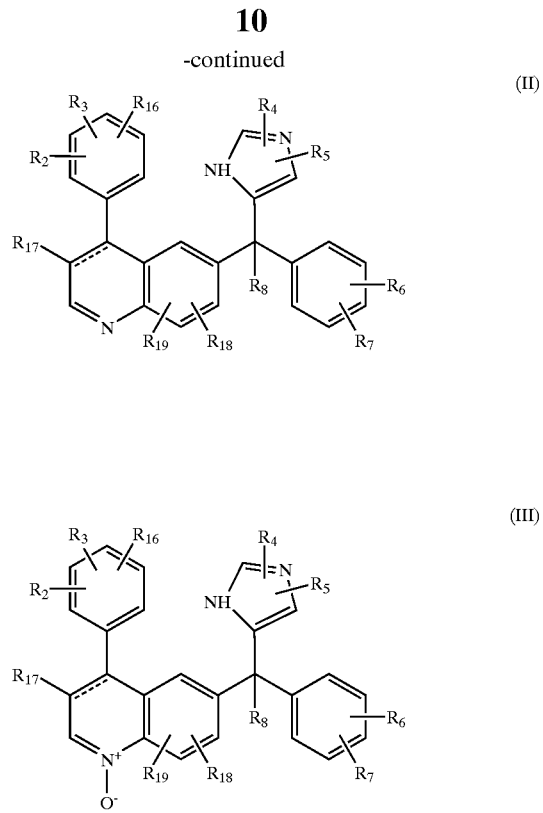

the pharmaceutically acceptable acid or base addition salts and the stereochemically isomeric forms thereof, wherein
the dotted line represents an optional bond;
X is oxygen or sulfur;
$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl,
or a radical of formula —Alk$^1$—C(=O)—R$^9$, —Alk$^1$—S(O)—R$^9$ or —Alk$^1$—S(O)$_2$—R$^9$,
wherein Alk$^1$ is $C_{1-6}$alkanediyl,
$R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;
$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or
when on adjacent positions $R^2$ and $R^3$ taken together may form a bivalent radical of formula

| —O—CH$_2$—O— | (a-1), |
| —O—CH$_2$—CH$_2$—O— | (a-2), |
| —O—CH=CH— | (a-3), |
| —O—CH$_2$—CH$_2$— | (a-4), |
| —O—CH$_2$—CH$_2$—CH$_2$— | (a-5), or |
| —CH=CH—CH=CH— | (a-6); |

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or
when on adjacent positions $R^6$ and $R^7$ taken together may form a bivalent radical of formula —O—CH$_2$—O— (c-1), or —CH=CH—CH=CH— (c-2);

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula —O—R$^{10}$ (b-1), —S—R$^{10}$ (b-2), —N—R$^{11}$R$^{12}$ (b-3), wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, or a radical or formula —Alk$^2$—OR$^{13}$ or —Alk$^2$—NR$^{14}$R$^{15}$;
$R^{11}$ is hydrogen, $C_{1-12}$alkyl, $Ar^1$ or $Ar^2C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl$C_{1-6}$alkyl, a natural amino acid, $Ar^1$carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk$^2$—OR$^{13}$ or —Alk$^2$—NR$^{14}$R$^{15}$;
wherein Alk$^2$ is $C_{1-6}$alkanediyl;
$R^{13}$ is hydrogen, $C_{1-6}$alkyl, $C_{1-6}$alkylcarbonyl, hydroxy$C_{1-6}$alkyl, $Ar^1$ or $Ar^2C_{1-6}$alkyl;
$R^{14}$ is hydrogen, $C_{1-6}$alkyl, $Ar^1$ or $Ar^2C_{1-6}$alkyl;
$R^{15}$ is hydrogen, $C_{1-6}$alkyl, $C_{1-6}$alkylcarbonyl, $Ar^1$ or $Ar^2C_{1-6}$alkyl;
$R^{17}$ is hydrogen, halo, cyano, $C_{1-6}$alkyl, $C_{1-6}$alkyloxycarbonyl, $Ar^1$;
$R^{18}$ is hydrogen, $C_{1-6}$alkyl, $C_{1-6}$alkyloxy or halo;
$R^{19}$ is hydrogen or $C_{1-6}$alkyl;
$Ar^1$ is phenyl or phenyl substituted with $C_{1-6}$alkyl, hydroxy, amino, $C_{1-6}$alkyloxy or halo; and
$Ar^2$ is phenyl or phenyl substituted with $C_{1-6}$alkyl, hydroxy, amino, $C_{1-6}$alkyloxy or halo.

In formulas (I), (II) and (III), $R^4$ or $R^5$ may also be bound to one of the nitrogen atoms in the imidazole ring. In that case the hydrogen on the nitrogen is replaced by $R^4$ or $R^5$ and the meaning of $R^4$ and $R^5$ when bound to the nitrogen is limited to hydrogen, $Ar^1$, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl, $C_{1-6}$alkylS(O)$_2C_{1-6}$alkyl.

As used in the foregoing definitions and hereinafter halo defines fluoro, chloro, bromo and iodo; $C_{1-6}$alkyl defines straight and branched chained saturated hydrocarbon radicals having from 1 to 6 carbon atoms such as, for example, methyl, ethyl, propyl, butyl, pentyl, hexyl and the like; $C_{1-8}$alkyl encompasses the straight and branched chained saturated hydrocarbon radicals as defined in $C_{1-6}$alkyl as well as the higher homologues thereof containing 7 or 8 carbon atoms such as, for example heptyl or octyl; $C_{1-12}$alkyl again encompasses $C_{1-8}$alkyl and the higher homologues thereof containing 9 to 12 carbon atoms, such as, for example, nonyl, decyl, undecyl, dodecyl; $C_{1-16}$alkyl again encompasses $C_{1-12}$alkyl and the higher homologues thereof containing 13 to 16 carbon atoms, such as, for example, tridecyl, tetradecyl, pentadecyl and hexadecyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof. The term "C(=O)" refers to a carbonyl group, "S(O)" refers to a sulfoxide and "S(O)$_2$" to a sulfon. The term "natural amino acid" refers to a natural amino acid that is bound via a covalent amide linkage formed by loss of a molecule of water between the carboxyl group of the amino acid and the amino group of the remainder of the molecule. Examples of natural amino acids are glycine, alanine, valine, leucine, isoleucine, methionine, proline, phenylanaline, tryptophan, serine, threonine, cysteine, tyrosine, asparagine, glutamine, aspartic acid, glutamic acid, lysine, arginine, histidine.

The pharmaceutically acceptable acid or base addition salts as mentioned hereinabove are meant to comprise the therapeutically active non-toxic acid and non-toxic base addition salt forms which the compounds of formulas (I), (II) and (III) are able to form. The compounds of formulas (I), (II) and (III) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formulas (I), (II) and (III) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formulas (I), (II) and (III) are able to form. Examples of such forms are e.g. hydrates, alcoholates and the like.

The term stereochemically isomeric forms of compounds of formulas (I), (II) and (III), as used hereinbefore, defines all possible compounds made up of the same atoms bonded by the same sequence of bonds but having different three-dimensional structures which are not interchangeable, which the compounds of formulas (I), (II) and (III) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereo-chemically isomeric forms of the compounds of formulas (I), (II) and (III) both in pure form or in admixture with each other are intended to be embraced within the scope of the present invention.

Some of the compounds of formulas (I), (II) and (III) may also exist in their tautomeric forms. Such forms although not explicitly indicated in the above formula are intended to be included within the scope of the present invention.

Whenever used hereinafter, the term "compounds of formulas (I), (II) and (III)" is meant to include also the pharmaceutically acceptable acid or base addition salts and all stereoisomeric forms.

Preferably the substituent $R^{18}$ is situated on the 5 or 7 position of the quinolinone moiety and substituent $R^{19}$ is situated on the 8 position when $R^{18}$ is on the 7-position.

Interesting compounds are these compounds of formula (I) wherein X is oxygen.

Also interesting compounds are these compounds of formula (I) wherein the dotted line represents a bond, so as to form a double bond.

Another group of interesting compounds are those compounds of formula (I) wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula —Alk$^1$—C(=O)—R$^9$, wherein Alk$^1$ is methylene and R$^9$ is $C_{1-8}$alkylamino substituted with $C_{1-6}$alkyloxycarbonyl.

Still another group of interesting compounds are those compounds of formula (I) wherein $R^3$ is hydrogen or halo; and $R^2$ is halo, $C_{1-6}$alkyl, $C_{2-6}$alkenyl, $C_{1-6}$alkyloxy, trihalomethoxy or hydroxy$C_{1-6}$alkyloxy.

A further group of interesting compounds are those compounds of formula (I) wherein $R^2$ and $R^3$ are on adjacent positions and taken together to form a bivalent radical of formula (a-1), (a-2) or (a-3).

A still further group of interesting compounds are those compounds of formula (I) wherein $R^5$ is hydrogen and $R^4$ is hydrogen or $C_{1-6}$alkyl.

Yet another group of interesting compounds are those compounds of formula (I) wherein $R^7$ is hydrogen; and $R^6$ is $C_{1-6}$alkyl or halo, preferably chloro, especially 4-chloro.

A particular group of compounds are those compounds of formula (I) wherein $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —NR$^{11}$R$^{12}$ wherein R$^{11}$ is hydrogen or $C_{1-12}$alkyl and R$^{12}$ is hydrogen, $C_{1-6}$alkyl, $C_{1-6}$alkyloxy, hydroxy, $C_{1-6}$alkyloxy$C_{1-6}$alkylcarbonyl, or a radical of formula —Alk$^2$—OR$^{13}$ wherein R$^{13}$ is hydrogen or $C_{1-6}$alkyl.

Preferred compounds are those compounds wherein R$^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula —Alk$^1$—C(=O)—R$^9$, wherein Alk$^1$ is methylene and R$^9$ is $C_{1-8}$alkylamino substituted with $C_{1-6}$alkyloxycarbonyl; R$^2$ is halo, $C_{1-6}$alkyl, $C_{2-6}$alkenyl, $C_{1-6}$alkyloxy, trihalomethoxy, hydroxy$C_{1-6}$alkyloxy or Ar$^1$; R$^3$ is hydrogen; R$^4$ is methyl bound to the nitrogen in 3-position of the imidazole; R$^5$ is hydrogen; R$^6$ is chloro; R$^7$ is hydrogen; R$^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —NR$^{11}$R$^{12}$ wherein R$^{11}$ is hydrogen or $C_{1-12}$alkyl and R$^{12}$ is hydrogen, $C_{1-6}$alkyl, $C_{1-6}$alkyloxy, $C_{1-6}$alkyloxy$C_{1-6}$alkylcarbonyl, or a radical of formula —Alk$^2$—OR$^{13}$ wherein R$^{13}$ is $C_{1-6}$alkyl; R$^{17}$ is hydrogen and R$^{18}$ is hydrogen.

Most preferred compounds are 4-(3-chlorophenyl)-6-[(4-chlorophenyl)hydroxy(1-methyl-1H-imidazol-5-yl)methyl]-1-ethyl-2(1H)-quinolinone;

6-[amino(4-chlorophenyl)-1-methyl-1H-imidazol-5-ylmethyl]-4-(3-chlorophenyl)-1-methyl-2(1H)-quinolinone;

6-[(4-chlorophenyl)hydroxy(1-methyl-1H-imidazol-5-yl)methyl]-4-(3-ethoxyphenyl)-1-methyl-2(1H)-quinolinone;

6-[(4-chlorophenyl)(1-methyl-1H-imidazol-5-yl)methyl]-4-(3-ethoxyphenyl)-1-methyl-2(1H)-quinolinone monohydrochloride.monohydrate;

6-[amino(4-chlorophenyl)(1-methyl-1H-imidazol-5-yl)methyl]-4-(3-ethoxyphenyl)-1-methyl-2(1H)-quinolinone, 6-amino(4-chlorophenyl)(1-methyl-1H-imidazol-5-yl)methyl]-1-methyl-4-(3-propyl-phenyl)-2(1H)-quinolinone; a stereoisomeric form thereof or a pharmaceutically acceptable acid or base addition salt; and in particular (+)-(R)-6-[amino(4-chlorophenyl)(1-methyl-1H-imidazol-5-yl)methyl]-4-(3-chloro-phenyl)-1-methyl-2(1H)-quinolinone (Compound 75 in Table 1 of the Experimental Part); or a pharmaceutically acceptable acid addition salt thereof.

Farnesyl protein transferase inhibitors can be formulated into pharmaceutical compositions as known in the art; for the compounds of formulas (I), (II) and (III) suitable examples can be found in WO-97/21701. To prepare the aforementioned pharmaceutical compositions, a therapeutically effective amount of the particular compound, optionally in addition salt form, as the active ingredient is combined in intimate admixture with pharmaceutically acceptable carriers, which may take a wide variety of forms depending on the form of preparation desired for administration.

These pharmaceutical compositions are, desirably as unitary dosage forms, administered orally, parenterally, percutaneously, rectally or topically for systemic action, which is preferred, or for topical action. In case of oral liquid pharmaceutical preparations, comprising solutions, suspensions, syrups, elixirs and emulsions, any of the usual pharmaceutical media, such as, for example, water, glycols, oils, alcohols and the like, may be employed, whereas in case of oral solid pharmaceutical preparations, comprising powders, pills, capsules and tablets, excipients such as starches, sugars, kaolin, lubricants, binders, disintegrating agents and the like may be employed. Because of their ease in administration, tablets and capsules represent the most advantageous oral unit dosage forms, in which case solid pharmaceutical carriers are obviously employed. In case of injectable pharmaceutical compositions, the carrier will usually comprise sterile water, at least in large part, though other ingredients, such as semipolair solvents, may be included, for example, to aid solubility. Examples of carriers for injectable solutions comprise saline solution, glucose solution or a mixture of saline and glucose solution. Injectable solutions containing compounds of the aforementioned formulas may also be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. For the preparation of injectable suspensions, appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on, as an ointment or as a gel. In case of pharmaceutical compositions for rectal administration, any of the usual excipients may be employed, comprising fat based and water soluble excipients, optionally combined with suitable additives, such as suspending or wetting agents. As appropriate compositions for topical application there may be cited all compositions usually employed for topically administering drugs e.g. creams, gellies, dressings, lotions, shampoos, tinctures, pastes, ointments, salves, ovules, powders, inhalations, nose sprays, eye drops and the like. Semisolid compositions such as salves, creams, gellies, ointments and the like will conveniently be used, but application of said compositions may be, for example, also by aerosol, e.g. with a propellant such as nitrogen, carbon dioxide, a freon, or without a propellant such as a pump spray or drops.

It is especially advantageous to formulate the aforementioned pharmaceutical compositions in unit dosage form for ease of administration and uniformity of dosage. Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, suppositories, ovules, wafers, injectable solutions or suspensions, teaspoonfuls, tablespoonfuls and the like, and segregated multiples thereof.

Preferably, a therapeutically effective amount of the pharmaceutical composition comprising a farnesyl protein transferase inhibitor is administered orally or parenterally. Said therapeutically effective amount is the amount that effectively sensitizes a tumor in a host to irradiation. On the basis of the current data, it appears that the pharmaceutical composition comprising (+)-(R)-6-[amino(4-chlorophenyl) (1-methyl-1H-imidazol-5-yl)methyl]-4-(3-chlorophenyl)-1-methyl-2(1H)-quinolinone (compound 75) as the activeingredient can be administered orally in an amount of from 10 up to 1500 mg/m² daily, either as a single dose or subdivided into more than one dose, or more particularly in an amount of from 100 to 1000 mg/m² daily.

Irradiation means ionizing radiation and in particular gamma radiation, especially that emitted by linear accelerators or by radionuclides that are in common use today. The irradiation of the tumor by radionuclides can be external or internal.

Preferably, the administration of the pharmaceutical composition commences up to one month, in particular up to 10 days or a week, before the irradiation of the tumor. Additionally, it is advantageous to fractionate the irradiation of the tumor and maintain the administration of the pharmaceutical composition in the interval between the first and the last irradiation session.

The amount of farnesyl protein transferase inhibitor, the dose of irradiation and the intermittence of the irradiation doses will depend on a series of parameters such as the type of tumor, its location, the patients' reaction to chemo- or radiotherapy and ultimately is for the physician and radiologists to determine in each individual case.

The present invention also concerns a method of cancer therapy for a host harboring a tumor comprising the steps of administering a radiation-sensitizing effective amount of a farnesyl protein transferase inhibitor before, during or after administering radiation to said host in the proximity to the tumor.

Examples of tumors which may be inhibited, but are not limited to, lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma, kidney carninoma, ovary carcinoma, bladder carcinoma and epidermal carcinoma.

EXPERIMENTAL PART

The following tables show the formulas of the compounds of formula (I), their physical data, and references to the examples in WO-97/21701 according to which the compounds in question may be prepared. In the pharmacological example, the radiation sensitizing effect of the compounds of formula (I) is illustrated.

TABLE 1

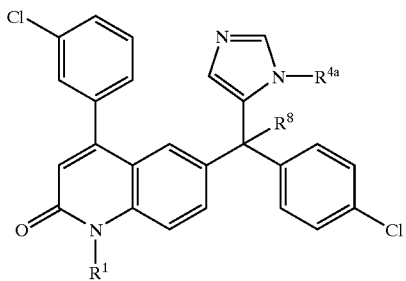

| Co. No. | Ex. No. | R¹ | R⁴ᵃ | R⁸ | Physical data |
|---|---|---|---|---|---|
| 3 | B.1 | $CH_3$ | $CH_3$ | OH | mp. 233.6° C. |
| 4 | B.3 | $CH_3$ | $CH_3$ | $OCH_3$ | mp. 140–160° C.; $.C_2H_2O_4.H_2O$ |
| 5 | B.6 | $CH_3$ | $CH_3$ | H | mp. 165° C.; $.C_2H_2O_4.H_2O$ |
| 6 | B.5 | $CH_3$ | $CH_2CH_3$ | H | mp. 180° C.; $.C_2H_2O_4.1/2H_2O$ |
| 7 | B.2 | H | $CH_3$ | H | mp. 260° C. |
| 8 | B.2 | H | $(CH_2)_3CH_3$ | OH | — |
| 9 | B.4 | $CH_3$ | $(CH_2)_3CH_3$ | OH | mp. 174° C. |
| 10 | B.3 | H | $CH_3$ | $OCH_2COOC_2H_5$ | mp. 185° C.; $.3/2C_2H_2O_4$ |
| 11 | B.3 | $CH_3$ | $CH_3$ | $O(CH_2)_2N(CH_3)_2$ | mp. 120° C. |
| 12 | B.7 | $CH_3$ | $CH_3$ | $CH_3$ | mp. 210° C.; $.C_2H_2O_4$ |
| 13 | B.7 | $CH_3$ | $CH_3$ | $CH_2CH_3$ | mp. 196° C.; $.C_2H_2O_4$ |
| 14 | B.13 | $CH_3$ | $CH_3$ | $NH_2$ | mp. 220° C. |
| 72 | B.13 | $CH_3$ | $CH_3$ | $NH_2$ | $.3/2$-(E)-$C_4H_4O_4$ |
| 73 | B.13 | $CH_3$ | $CH_3$ | $NH_2$ | .2HCl |
| 74 | B.8b | $CH_3$ | $CH_3$ | $NH_2$ | (A) |
| 75 | B.8b | $CH_3$ | $CH_3$ | $NH_2$ | (+) |
| 15 | B.3 | $CH_3$ | $CH_3$ | $O(CH_2)_3OH$ | mp. 135° C. |
| 16 | B.3 | $CH_3$ | $CH_3$ | $O(CH_2)_2CH_3$ | mp. 180° C.; $.C_2H_2O_4.3/2(H_2O)$ |
| 17 | B.3 | $CH_3$ | $CH_3$ | $O(CH_2)_2O-C_6H_5$ | mp. 144° C.; $.3/2(C_2H_2O_4)$ |
| 18 | B.2 | H | $CH(CH_3)_2$ | OH | — |
| 19 | B.4 | $CH_3$ | $CH(CH_3)_2$ | OH | mp. 254° C. |
| 20 | B.2 | H | $(CH_2)_2OCH_3$ | OH | mp. 112° C. |
| 21 | B.4 | $CH_3$ | $(CH_2)_2OCH_3$ | OH | mp. 192° C. |
| 22 | B.3 | $CH_3$ | $CH_3$ | $O(CH_2)_2OH$ | mp. 198° C. |
| 23 | B.8a | $CH_3$ | $CH_3$ | OH | mp. 150–200° C.; (A); $.C_2H_2O_4$ |
| 24 | B.8a | $CH_3$ | $CH_3$ | OH | mp. 150–200° C.; (B); $.C_2H_2O_4$ |
| 25 | B.11 | $CH_3$ | $CH_3$ | $CH_2-CN$ | mp. 154° C. |
| 27 | B.2 | H | $(CH_2)_3OCH_3$ | OH | — |
| 28 | B.4 | $CH_3$ | $(CH_2)_3OCH_3$ | OH | mp. 196° C.; $.H_2O$ |
| 29 | B.3 | $CH_3$ | $CH_3$ | $O(CH_2)_3OCH_2CH_3$ | mp. 105° C.; $.3/2(H_2O)$ |
| 31 | B.2 | H | $CH_3$ | OH | >260° C. |
| 32 | B.6 | $CH_3$ | $(CH_2)_2OCH_3$ | H | mp. 140° C.; $.3/2(C_2H_2O_4)$ |
| 33 | B.6 | $CH_3$ | $(CH_2)_3OCH_3$ | H | mp. 180° C.; .HCl |
| 56 | B.12 | $CH_3$ | $CH_3$ | $-NHCOCH_3$ | $.C_2H_2O_4$ |
| 58 | B.11 | $CH_3$ | $CH_3$ | $-CH_2COOCH_2CH_3$ | $.C_2H_2O_4.3/2(H_2O)$ |
| 60 | B.11 | $CH_3$ | $CH_3$ | 1-imidazolyl | — |
| 61 | B.21 | $CH_3$ | $CH_3$ | $-NH-CH_3$ | mp. 164° C. |
| 65 | B.2 | H | $(CH_2)_3SOCH_3$ | OH | $.H_2O$ |
| 66 | B.13 | $CH_3$ | $CH_3$ | $-N(CH_3)_2$ | $.2C_2H_2O_4.H_2O$ mp. 160° C. |
| 67 | B.13 | $CH_3$ | $CH_3$ | $-NH-(CH_2)_2OCH_3$ | mp. 216° C. |
| 68 | B.13 | $CH_3$ | $CH_3$ | $-NH-(CH_2)_2-OH$ | — |
| 69 | B.7 | $CH_3$ | $CH_3$ | $-CH_2Cl$ | $.2C_2H_2O_4$ mp. 220° C. |
| 70 | B.7 | $CH_3$ | $CH_3$ | $-CH_2Br$ | — |
| 71 | * | $CH_3$ | $CH_3$ | $-CH_2OH$ | $.2C_2H_2O_4$ |
| 76 | B.4 | $-(CH_2)_2OCH_3$ | $CH_3$ | OH | mp. 150° C. |
| 77 | * | $CH_3$ | $CH_3$ | $-CH_2OCH_3$ | $.2C_2H_2O_4$ mp. 166° C. |

TABLE 1-continued

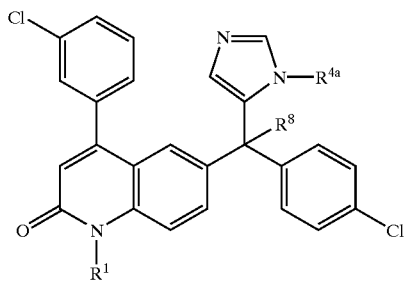

| Co. No. | Ex. No. | R¹ | R⁴ᵃ | R⁸ | Physical data |
|---|---|---|---|---|---|
| 78 | B.13 | $CH_3$ | $CH_3$ | —NH—$OCH_3$ | mp. 170° C. |
| 79 | B.20 | $CH_3$ | $CH_3$ | —NH—$CONH_2$ | $.2H_2O$ |
| 80 | ** | $CH_3$ | $CH_3$ | —$CH_2CONH_2$ | — |
| 81 | B.13 | $CH_3$ | $CH_3$ | —NH—OH | — |
| 82 | B.13 | $CH_3$ | $CH_3$ | —$NH(CH_2)_2N(CH_3)_2$ | — |
| 83 | B.4 | $(CH_2)_2N(CH_3)_2$ | $CH_3$ | OH | $.3/2C_2H_2O_4$ $.3/2H_2O$ mp. 200 ° C. |
| 84 | * | $CH_3$ | $CH_3$ | —$CH_2N(CH_3)_2$ | $.C_2H_2O_4$ mp. 210° C. |
| 85 | B.4 | $CH_3$ | $CH_3$ | —$N(CH_3)_2$ | — |
| 86 | B.4 | $CH_3$ | $CH_3$ | $NHCOCH_2N(CH_3)_2$ | — |
| 87 | B.4 | $CH_3$ | $CH_3$ | —$NH(CH_2)_9CH_3$ | — |
| 88 | B.4 | $CH_3$ | $CH_3$ | —$NH(CH_2)_2NH_2$ | — |
| 89 | B.20 | $CH_3$ | $CH_3$ | —$NHCOCH_2OCH_3$ | .HCl mp. 220° C. |
| 90 | B.6 | $CH_3$ | $CH_3$ | H | — |
| 91 | B.20 | $CH_3$ | $CH_3$ | —$NHCOCH_2C_6H_5$ | $.C_2H_2O_4.H_2O$ mp. 170° C. |
| 92 | B.20 | $CH_3$ | $CH_3$ | —$NHCOC_6H_5$ | mp. 242° C. |
| 93 | B.20 | $CH_3$ | $CH_3$ | —$NHCOCONH_2$ | $.C_2H_2O_4.H_2O$ mp. 186° C. |
| 94 | B.13 | $CH_3$ | $CH_3$ | —$NHC_6H_5$ | mp. 165° C. |

*: prepared by functional-group transformation of compound 70
**: prepared by functional-group transformation of compound 25

TABLE 2

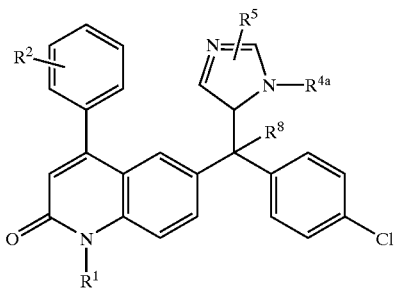

| Co. No. | Ex. No. | R¹ | R² | R⁴ᵃ | R⁵ | R⁸ | Physical data |
|---|---|---|---|---|---|---|---|
| 1 | B.1 | $CH_3$ | H | $CH_3$ | H | OH | mp. >250° C. |
| 2 | B.5 | $CH_3$ | H | $CH_3$ | H | H | mp. 100–110° C. |
| 26 | B.1 | $CH_3$ | 3-Cl | $CH_3$ | 2-$CH_3$ | OH | mp. 200° C. |
| 30 | B.6 | $CH_3$ | 3-Cl | $CH_3$ | 2-$CH_3$ | H | mp. 120–140° C.; $.3/2(C_2H_2O_4).H_2O$ |
| 34 | B.1 | $CH_3$ | 3-O—$CH_2$—$CH_3$ | $CH_3$ | H | OH | mp. 190° C. |
| 35 | B.6 | $CH_3$ | 3-O—$CH_2$—$CH_3$ | $CH_3$ | H | H | mp. 160–180° C.; $.HCl.H_2O$ |
| 36 | B.1 | $CH_3$ | 3-O—$CH_3$ | $CH_3$ | H | OH | mp. 210° C. |
| 37 | B.1 | $CH_3$ | 3-O—$(CH_2)_2$—$CH_3$ | $CH_3$ | H | OH | mp. 150–160° C. |
| 38 | B.1 | $CH_3$ | 3-O—$(CH_2)_3$—$CH_3$ | $CH_3$ | H | OH | mp. 150–160° C. |

TABLE 2-continued

| Co. No. | Ex. No. | R¹ | R² | R⁴ᵃ | R⁵ | R⁸ | Physical data |
|---|---|---|---|---|---|---|---|
| 49 | B.1 | CH₃ | 4-O—CH₂—CH₃ | CH₃ | H | OH | mp. 184.2° C. |
| 50 | B.1 | CH₃ | 3-O—CH—(CH₃)₂ | CH₃ | H | OH | mp. 147.1° C. |
| 51 | B.6 | CH₃ | 3-O—(CH₂)₃—CH₃ | CH₃ | H | H | mp. 164.2° C.; .3/2(C₂H₂O₄) |
| 52 | B.6 | CH₃ | 3-O—(CH₂)₂—CH₃ | CH₃ | H | H | .3/2(C₂H₂O₄) |
| 53 | B.6 | CH₃ | 3-O—CH—(CH₃)₂ | CH₃ | H | H | mp. 133.9° C.; .C₂H₂O₄.H₂O |
| 54 | B.14 | CH₃ | 3-OH | CH₃ | H | OH | — |
| 64 | B.10 | CH₃ | 3-OH | CH₃ | H | OH | .HCl.H₂O |
| 55 | B.6 | CH₃ | 3-OH | CH₃ | H | H | mp. >250° C. |
| 57 | B.1 | CH₃ | 2-OCH₂CH₃ | CH₃ | H | OH | — |
| 59 | B.13 | CH₃ | 3-OCH₂CH₃ | CH₃ | H | NH₂ | — |
| 95 | B.8a | CH₃ | 3-OCH₂CH₃ | CH₃ | H | NH₂ | (A) |
| 96 | B.8a | CH₃ | 3-OCH₂CH₃ | CH₃ | H | NH₂ | (B) |
| 62 | B.15 | CH₃ | 3-O(CH₂)₂N(CH₃)₂ | CH₃ | H | OH | — |
| 63 | B.11 | CH₃ | 3-O(CH₂)₂—OH | CH₃ | H | OH | — |
| 97 | B.1 | CH₃ | 3-CH₂CH₃ | CH₃ | H | OH | — |
| 98 | B.13 | CH₃ | 3-CH₂CH₃ | CH₃ | H | NH₂ | mp. 240° C. |
| 99 | B.1 | CH₃ | 3-(CH₂)₂CH₃ | CH₃ | H | OH | — |
| 100 | B.13 | CH₃ | 3-(CH₂)₂CH₃ | CH₃ | H | NH₂ | — |
| 101 | * | CH₃ | 3-O—(CH₂)₂OCH₃ | CH₃ | H | OH | .3/2(C₂H₂O₄) mp. 193° C. |
| 102 | B.1 | CH₃ | 3-CH₃ | CH₃ | H | OH | mp. >250° C. |
| 103 | B.13 | CH₃ | 3-CH₃ | CH₃ | H | NH₂ | — |
| 104 | B.1 | CH₃ | 3-Br | CH₃ | H | OH | — |
| 105 | B.13 | CH₃ | 3-Br | CH₃ | H | NH₂ | — |
| 106 | B.1 | CH₃ | 3-O—CF₃ | CH₃ | H | OH | — |
| 107 | B.13 | CH₃ | 3-O—CF₃ | CH₃ | H | NH₂ | mp. 168° C. |
| 108 | B.1 | CH₃ | 3-C₆H₅ | CH₃ | H | OH | — |
| 109 | B.13 | CH₃ | 3-C₆H₅ | CH₃ | H | NH₂ | — |
| 110 | B.1 | CH₃ | 3-F | CH₃ | H | OH | — |
| 111 | B.13 | CH₃ | 3-F | CH₃ | H | NH₂ | mp. >250° C. |
| 112 | B.1 | CH₃ | 3-(E)-CH=CH—CH₃ | CH₃ | H | OH | mp. >250° C. |
| 113 | B.2 | H | 3-Cl | CH₃ | 3-Cl | OH | — |
| 114 | B.4 | CH₃ | 3-Cl | CH₃ | 3-Cl | OH | — |
| 115 | B.1 | CH₃ | 3-Cl | H | 3-CH₃ | OH | — |
| 116 | B.4 | CH₃ | 3-Cl | CH₃ | 3-CH₃ | OH | — |
| 117 | ** | CH₃ | 3-CN | CH₃ | H | OH | — |
| 160 | B.1 | CH₃ | 3-CF₃ | CH₃ | H | OH | — |

*: prepared by functional-group transformation of compound 54
**: prepared by functional-group transformation of compound 104

TABLE 3

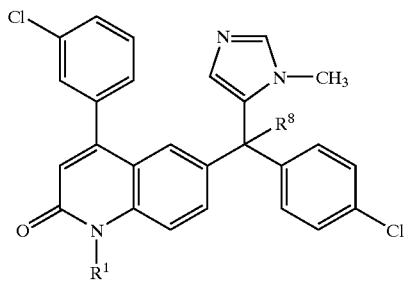

| Co. No. | Ex. No. | R¹ | R⁸ | Physical data |
|---|---|---|---|---|
| 39 | B.4 | CH₂CONHCH(COOCH₃) (CH₂CH(CH₃)₂) | H | mp. 240° C. (S) |
| 40 | B.4 | CH₂-2-quinolinyl | H | mp. 240° C.; .2 HCl |
| 41 | B.4 | CH₂CONHCH(COOCH₃) (CH₂CH(CH₃)₂) | OH | mp. >260° C. (S) |

TABLE 4

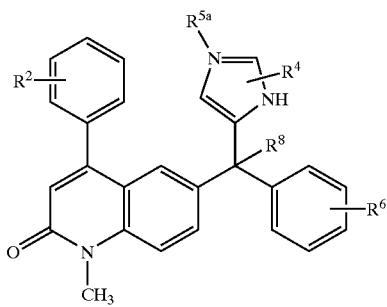

| Co. No. | Ex. No. | R² | R⁴ | R⁵ᵃ | R⁶ | R⁸ | Physical data |
|---|---|---|---|---|---|---|---|
| 42 | B.6 | H | H | H | 4-Cl | H | mp. 170° C.; .C₂H₂O₄.1/2 H₂O |
| 43 | B.10 | H | H | H | 4-Cl | OH | mp. 180° C.; .H₂O |
| 44 | B.5 | H | H | CH₃ | 4-Cl | H | mp. 152° C. |
| 45 | B.6 | 3-Cl | H | H | 4-Cl | H | mp. 175° C.; .C₂H₂O₄ |
| 46 | B.5 | 3-Cl | H | CH₂CH₃ | 4-Cl | H | mp. 132° C.; .C₂H₂O₄ |
| 47 | B.5 | 3-Cl | H | CH₃ | 4-Cl | H | mp. 115° C.; .3/2 C₂H₂O₄ |
| 48 | B.9 | 3-Cl | H | CH₃ | 4-Cl | OH | mp. 230° C. |
| 118 | B.4 | 3-Cl | 3-CH₃ | CH₃ | 4-Cl | OH | mp. 222° C. |

TABLE 5

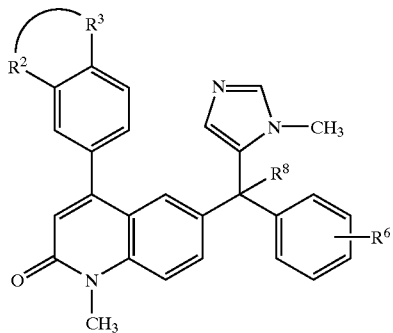

| Co. No. | Ex. No. | -R²-R³- | R⁶ | R⁸ |
|---|---|---|---|---|
| 119 | B.1 | —O—CH₂—O— | 4-Cl | OH |
| 120 | B.13 | —O—CH₂—O— | 4-Cl | NH₂ |

TABLE 5-continued

| Co. No. | Ex. No. | -R² -R³- | R⁶ | R⁸ |
|---|---|---|---|---|
| 121 | B.1 | —O—CH₂—CH₂—O— | 4-Cl | OH |
| 122 | B.13 | —O—CH₂—CH₂—O— | 4-Cl | NH₂ |
| 123 | B.1 | —O—CH=CH— | 4-Cl | OH |

TABLE 6

| Co. No. | Ex. No. | X | ----- | R² | R³ | R¹⁶ | R⁸ | Physical data |
|---|---|---|---|---|---|---|---|---|
| 124 | B.1 | O | double | 3-OCH₃ | 4-OCH₃ | 5-OCH₃ | OH | mp. 230° C. |
| 125 | B.13 | O | double | 3-OCH₃ | 4-OCH₃ | 5-OCH₃ | NH₂ | mp. 218° C. .C₂H₂O₄ |
| 126 | B.1 | O | single | 3-Cl | H | H | OH | mp. 160° C. |
| 127 | B.1 | O | single | 3-Cl | H | H | OH | — |
| 128 | B.16 | S | double | 3-Cl | H | H | H | — |

TABLE 7

| Co. No. | Ex. No. | R¹ | R¹⁷ | R¹⁸ | R¹⁹ | R⁸ | Physical data |
|---|---|---|---|---|---|---|---|
| 129 | B.17 | H | CN | H | H | H | — |
| 130 | B.4 | CH₃ | CN | H | H | H | mp. 202° C. |

TABLE 7-continued

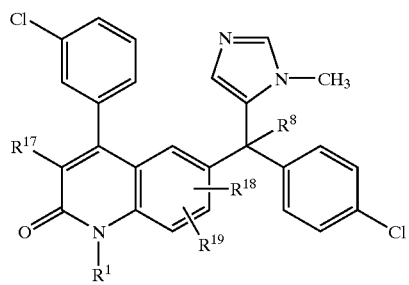

| Co. No. | Ex. No. | R¹ | R¹⁷ | R¹⁸ | R¹⁹ | R⁸ | Physical data |
|---|---|---|---|---|---|---|---|
| 131 | B.17 | H | CN | H | H | OH | — |
| 132 | B.4 | CH₃ | CN | H | H | OH | — |
| 133 | B.17 | H | CN | H | H | —CH₂CN | — |
| 134 | B.4 | CH₃ | CN | H | H | —CH₂CN | mp. 138° C. |
| 135 | B.18 | H | CH₃ | H | H | OH | — |
| 136 | B.4 | CH₃ | CH₃ | H | H | OH | — |
| 137 | B.13 | CH₃ | CH₃ | H | H | NH₂ | mp. >250° C. |
| 138 | B.18 | H | C₆H₅ | H | H | H | — |
| 139 | B.4 | CH₃ | C₆H₅ | H | H | H | .3/2(C₂H₂O₄) mp. 180° C. |
| 140 | B.18 | H | C₆H₅ | H | H | OH | — |
| 141 | B.4 | CH₃ | C₆H₅ | H | H | OH | — |
| 142 | B.13 | CH₃ | C₆H₅ | H | H | NH₂ | — |
| 143 | B.13 | CH₃ | Cl | H | H | NH₂ | — |
| 144 | B.17 | H | —COOCH₂CH₃ | H | H | OH | — |
| 145 | B.4 | CH₃ | —COOCH₂CH₃ | H | H | OH | — |
| 146 | B.1 | CH₃ | H | 8-CH₃ | H | OH | — |
| 147 | B.13 | CH₃ | H | 8-CH₃ | H | NH₂ | .H₂O |
| 148 | B.1 | CH₃ | H | 7-Cl | H | OH | — |
| 149 | B.1 | CH₃ | H | 7-CH₃ | H | OH | — |
| 150 | B.1 | CH₃ | H | 5-CH₃ | H | OH | — |
| 151 | B.1 | CH₃ | H | 8-OCH₃ | H | OH | — |
| 161 | B.1 | CH₃ | H | 7-CH₃ | 8-CH₃ | OH | mp. 255° C. |

TABLE 8

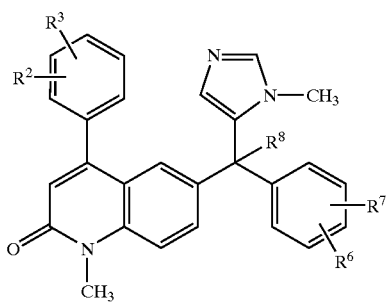

| Co. No. | Ex. No. | R² | R³ | R⁶ | R⁷ | R⁸ | Physical data |
|---|---|---|---|---|---|---|---|
| 152 | B.1 | 3-OCH₂CH₃ | H | 4-OCH₂CH₃ | H | OH | .3/2(C₂H₂O₄) |
| 153 | B.1 | 3-Cl | H | H | H | OH | — |
| 154 | B.1 | 3-Cl | H | 4-CH₃ | H | OH | — |
| 155 | B.1 | 3-Cl | H | 4-OCH₃ | H | OH | — |
| 156 | B.1 | 3-Cl | H | 4-CF₃ | H | OH | — |
| 157 | B.1 | 3-Cl | H | 2-Cl | 4-Cl | OH | — |
| 158 | B.1 | 3-Cl | 5-Cl | 4-Cl | H | OH | — |
| 159 | B.1 | 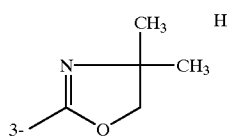 | H | 4-Cl | H | OH | — |

TABLE 8-continued

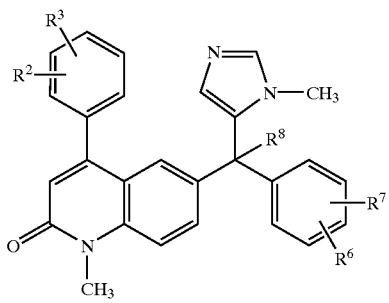

| Co. No. | Ex. No. | R² | R³ | R⁶ | R⁷ | R⁸ | Physical data |
|---|---|---|---|---|---|---|---|
| 162 | B.1 | 3-Cl | H | 4-S—CH₃ | H | OH | mp. 169° C. .C₂H₂O₄.H₂O; |
| 163 | B.1 | 3-Cl | H | 4-N(CH₃)₂ | H | OH | mp. decomposes > 172° C. |
| 164 | B.1 | 3-Cl | H | —CH=CH—CH=CH—* | | OH | .C₂H₂O₄ |

*: $R^6$ and $R^7$ taken together to form a bivalent radical between positions 3 and 4 on the phenyl moiety

PHARMACOLOGICAL EXAMPLE 1

Male athymic nude mice weighing approximately 22 to 25 g were inoculated subcutaneously in the inguinal region with $1 \times 10^6$ of LoVo human colon tumor cells (LoVo cells) on day 0. After three weeks to allow tumors to become established (diameter approximately 0.5 to 1 cm), treatment was started with solvent or compound 75 via the oral route, and either with or without a single shot irradiation on day 32. Parameters for activity were tumor growth rate and weight of the tumors at day 42.

Compound 75 was dissolved in water and acidified with 1 N HCl solution to pH 2.5 and administered orally (po) as 0.1 ml of compound solution per 10 g mouse body weight twice daily (bid). The dose administered was either 50 or 100 mg compound per kg bodyweight; treatment either preceded irradiation (days 22–32), followed irradiation (days 32–42) or continued throughout the duration of the experiment (days 22–42).

Irradiation treatment consisted of a single dose of radiation on day 32 with a dose of 7 Gy that stabilized tumor growth in untreated animals, i.e. a dose that stopped the increase in tumor volume, but did not cause any reduction in its size either.

The following table (Table 9) shows each of the arms that were evaluated in the experiment. In each arm of the experiment 16 animals were included. The column 'tumor (g)' contains the median of the tumor weight of the animals sacrificed at day 42 of the experiment. FIGS. 1 and 2 represent the observed data in graphical form.

FIG. 1 shows the distribution of the tumor weights (g) of the test animals receiving 50 mpk of test compound (po, bid).

FIG. 2 shows the distribution of the tumor weights (g) of the test animals receiving 100 mpk of test compound (po, bid).

The gray box in the figures depicts the 25–75 percentiles, the solid black line therein represents the median, the lines extending from the gray box depict the 10–90 percentiles and the black dots represent the outliers. The Roman numbers correspond to the groups of test animals as identified in Table 9.

From a statistical analysis of the data it follows that treatment with compound 75 (both 50 and 100 mpk) potentiates the effect of irradiation, more in particular that pre-treatment with compound 75 (both 50 and 100 mpk) and irradiation reduces tumor weight in a statistically significant manner (when compared to irradiation alone).

TABLE 9

| Group | Compound 75 | treatment schedule | Irradiation | tumor (g) |
|---|---|---|---|---|
| I | solvent | day 22–42 | none | 0.475 |
| II | 50 mpk | day 22–42 | none | 0.255 |
| III | 50 mpk | day 22–32 | none | 0.273 |
| IV | 50 mpk | day 32–42 | none | 0.295 |
| V | 100 mpk | day 22–42 | none | 0.205 |
| VI | 100 mpk | day 22–32 | none | 0.234 |
| VII | 100 mpk | day 32–42 | none | 0.277 |
| VIII | 50 mpk | day 22–42 | 7 Gy | 0.207 |
| IX | 50 mpk | day 22–32 | 7 Gy | 0.156 (p = 0.03)* |
| X | 50 mpk | day 32–42 | 7 Gy | 0.259 |
| XI | 100 mpk | day 22–42 | 7 Gy | 0.164 (p = 0.0317)* |
| XII | 100 mpk | day 22–32 | 7 Gy | 0.141 (p = 0.0022)* |
| XIII | 100 mpk | day 32–42 | 7 Gy | 0.214 |
| XIV | Solvent | day 22–42 | 7 Gy | 0.256 |

*Mann-Whitney U test vs Group XIV (radiotherapy only)

EXAMPLE 2

Radioresistant human glioma cell lines (SF763, U87, U251) were treated with compound 75, 48 h prior to irradiation (2 Gy). The dose administered was 0.4 nM for U251 and 2 nM for SF763 and U87.

Applying compound 75 to the cells dramatically reduced the surviving of the cells after irradiation: for SF763 and U87, a decrease of surviving fraction of about 55% was demonstrated, whereas for U251, the decrease was 25%.

These results demonstrate that treatment with compound 75 resensitizes radioresistant cells to irradiation.

What is claimed is:

1. A method for sensitizing a tumor in a host to irradiation comprising the steps of:

administering a radiation-sensitizing effective amount of a farnesyl protein transferase inhibitor before, during or after irradiation; and administering radiation to said host in the proximity to the tumor wherein said farnesyl protein transferase inhibitor is a compound of formula (I), or a compound of formula (II) or (III) which is metabolized in vivo to a compound of formula (I), said compounds being represented by:

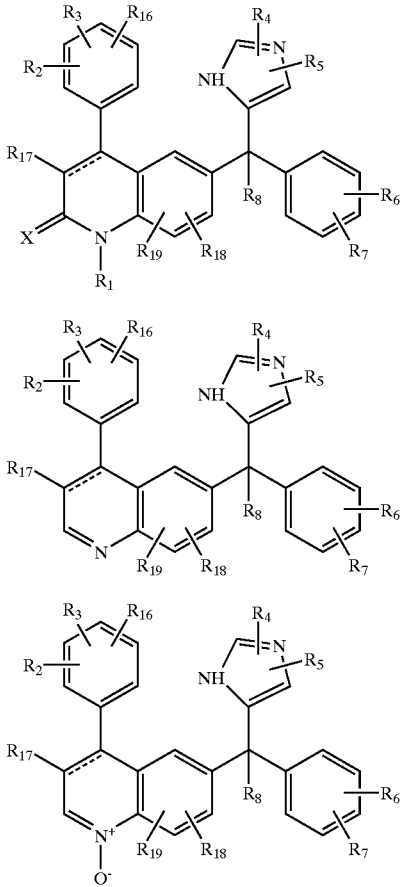

or a steroisomeric form thereof, or a pharmaceutically acceptable acid or base addition salt thereof wherein in formula (I), (II), or (III) the dotted line represents an optional bond and wherein X is oxygen or sulfur;

$R^1$ is hydrogen, $C_{1-12}$alkyl, $Ar^1$, $Ar^2C_{1-6}$alkyl, quinolinylC$_{1-6}$alkyl, pyridyl-C$_{1-6}$alkyl, hydroxyC$_{1-6}$alkyl, C$_{1-6}$alkyloxyC$_{1-6}$alkyl, mono- or di(C$_{1-6}$alkyl)-aminoC$_{1-6}$alkyl, aminoC$_{1-6}$alkyl, or a radical of formula —Alk$^1$—C(=O)—R$^9$, —Alk$^1$—S(O)R$^9$ or —Alk$^1$—S(O)$_2$—R$^9$, wherein Alk$^1$ is C$_{1-6}$alkanediyl, $R^9$ is hydroxy, C$_{1-6}$alkyl, C$_{1-6}$alkyloxy, amino, C$_{1-8}$alkylamino or C$_{1-8}$alkylamino substituted with C$_{1-6}$alkyloxycarbonyl, $R^2$, $R^3$ and $R^{16}$ each independently are hydrogen, hydroxy, halo, cyano, C$_{1-6}$alkyl, C$_{1-6}$alkyloxy, hydroxyC$_{1-6}$alkyloxy, C$_{1-6}$alkyloxyC$_{1-6}$alkyloxy, amino-C$_{1-6}$alkyloxy, mono- or di(C$_{1-6}$alkyl)aminoC$_{1-6}$alkyloxy, Ar$^1$, Ar$^2$C$_{1-6}$alkyl, Ar2oxy, Ar$^2$C$_{1-6}$alkyloxy, hydroxycarbonyl, C$_{1-6}$alkyloxycarbonyl, trihalomethyl, trihalomethoxy, C$_{2-6}$alkenyl, 4,4-dimethyloxazolyl; or when on adjacent positions R$^2$ and R$^3$ taken together may form a bivalent radical of formula —O—CH$_2$—O— (a-1), —O—CH$_2$—CH$_2$—O— (a-2), —O—CH=CH— (a-3), —O—CH$_2$—CH$_2$— (a-4), —O—CH$_2$—CH$_2$—CH$_2$— (a-5), or —CH=CH—CH=CH— (a-6);

$R^4$ and $R^5$ each independently are hydrogen, halo, Ar$^1$, C$_{1-6}$alkyl, hydroxy-C$_{1-6}$alkyl, C$_{1-6}$alkyloxyC$_{1-6}$alkyl, C$_{1-6}$alkyloxy, C$_{1-6}$alkylthio, amino, hydroxycarbonyl, C$_{1-6}$alkyloxycarbonyl, C$_{1-6}$alkylS(O)C$_{1-6}$alkyl or C$_{1-6}$alkylS(O)$_2$C$_{1-6}$alkyl;

$R^6$ and $R^7$ each independently are hydrogen, halo, cyano, C$_{1-6}$alkyl, C$_{1-6}$alkyloxy, Ar$^2$oxy, trihalomethyl, C$_{1-6}$alkylthio, di(C$_{1-6}$alkyl)amino, or when on adjacent positions R$^6$ and R$^7$ taken together may form a bivalent radical of formula —O—CH$_2$—O— (c-1), or —CH=CH—CH=CH— (c-2);

$R^8$ is hydrogen, C$_{1-6}$alkyl, cyano, hydroxycarbonyl, C$_{1-6}$alkyloxycarbonyl, C$_{1-6}$alkylcarbonylC$_{1-6}$alkyl, cyanoC$_{1-6}$alkyl, C$_{1-6}$alkyloxycarbonylC$_{1-6}$alkyl, carboxyC$_{1-6}$alkyl, hydroxyC$_{1-6}$alkyl, aminoC$_{1-6}$alkyl, mono- or di(C$_{1-6}$alkyl)-aminoC$_{1-6}$alkyl, imidazolyl, haloC$_{1-6}$alkyl, C$_{1-6}$alkyloxyC$_{1-6}$alkyl, aminocarbonylC$_{1-6}$alkyl, or a radical of formula —O—R$^{10}$ (b-1), —S—R$^{10}$ (b-2), —N—R$^{11}$R$^{12}$ (b-3), wherein R$^{10}$ is hydrogen, C$_{1-6}$alkyl, C$_{1-6}$alkylcarbonyl, Ar$^1$, Ar$^2$C$_{1-6}$alkyl, C$_{1-6}$alkyloxycarbonylC$_{1-6}$alkyl a radical or formula —Alk$^2$—OR$^{13}$ or —Alk$^2$—NR$^{14}$R$^{15}$;

R$^{11}$ is hydrogen, C$_{1-12}$alkyl, Ar$^1$ or Ar$^2$C$_{1-6}$alkyl;

R$^{12}$ is hydrogen, C$_{1-6}$alkyl, C$_{1-6}$alkylcarbonyl, C$_{1-6}$alkyloxycarbonyl, C$_{1-6}$alkylaminocarbonyl, Ar$^1$, Ar$^2$C$_{1-6}$alkyl, C$_{1-6}$alkylcarbonyl-C$_{1-6}$alkyl, a natural amino acid, Ar$^1$carbonyl, Ar$^2$C$_{1-6}$alkylcarbonyl, aminocarbonylcarbonyl, C$_{1-6}$alkyloxy-C$_{1-6}$alkylcarbonyl, hydroxy, C$_{1-6}$alkyloxy, aminocarbonyl, di(C$_{1-6}$alkyl)aminoC$_{1-6}$alkylcarbonyl, amino, C$_{1-6}$alkylamino, C$_{1-6}$alkylcarbonylamino, or a radical of formula —Alk$^2$—OR$^{13}$ or —Alk$^2$—NR$^{14}$R$^{15}$;

wherein Alk$^2$ is C$_{1-6}$alkanediyl;

R$^{13}$ is hydrogen, C$_{1-6}$alkyl, C$_{1-6}$alkylcarbonyl hydroxyC$_{1-6}$alkyl, Ar$^1$ or Ar$^2$C$_{1-6}$alkyl;

R$^{14}$ is hydrogen, C$_{1-6}$alkyl, Ar$^1$ or Ar$^2$C$_{1-6}$alkyl;

$R^{15}$ is hydrogen, $C_{1-6}$alkyl, $C_{1-6}$alkylcarbonyl, $Ar^1$ or $Ar^2C_{1-6}$alkyl;

$R^{17}$ is hydrogen, halo, cyano, $C_{1-6}$alkyl, $C_{1-6}$alkyloxycarbonyl, $Ar^1$;

$R^{18}$ is hydrogen, $C_{1-6}$alkyl, $C_{1-6}$alkyloxy or halo;

$R^{19}$ is hydrogen or $C_{1-6}$alkyl;

$Ar^1$ is phenyl or phenyl substituted with $C_{1-6}$alkyl, hydroxy, amino, $C_{1-6}$alkyloxy or halo; and $Ar^2$ is phenyl or phenyl substituted with $C_{1-6}$alkyl, hydroxy, amino, $C_{1-6}$alkyloxy or halo.

2. The method of claim 1 wherein said farnesyl protein transferase inhibitor is a compound of formula (I) and wherein X is oxygen.

3. The method of claim 1 wherein said farnesyl protein transferase inhibitor is a compound of formula (I) and wherein the dotted line represents a bond.

4. The method of claim 1 wherein said farnesyl protein transferase inhibitor is a compound of formula (I) and wherein $R^1$ is hydrogen, $C_{1-6}$alkyl, $C_{1-6}$alkyloxy-$C_{1-6}$alkyl or mono- or di($C_{1-6}$alkyl)amino$C_{1-6}$alkyl.

5. The method of claim 1 wherein said farnesyl protein transferase inhibitor is a compound of formula (I) and wherein $R^3$ is hydrogen and $R^2$ is halo, $C_{1-6}$alkyl, $C_{2-6}$alkenyl, $C_{1-6}$alkyloxy, trihalomethoxy or hydroxy$C_{1-6}$alkyloxy.

6. The method of claim 1 wherein said farnesyl protein transferase inhibitor is a compound of formula (I) and wherein $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —$NR^{11}R^{12}$ wherein $R^{11}$ is hydrogen or $C_{1-12}$alkyl and $R^{12}$ is hydrogen, $C_{1-6}$alkyl, $C_{1-6}$alkyloxy, $C_{1-6}$alkyloxy$C_{1-6}$alkylcarbonyl, hydroxy, or a radical of formula —$Alk^2$—$OR^{13}$ wherein $R^{13}$ is hydrogen or $C_{1-6}$alkyl.

7. The method of claim 1 wherein the compound is selected from the group consisting of:

4-(3-chlorophenyl)-6-[(4-chlorophenyl)hydroxy(1-methyl-1H-imidazol-5-yl)methyl]-1-methyl-2(1H)-quinolinone, 6-[amino(4-chlorophenyl)-1-methyl-1H-imidazol-5-ylmethyl]-4-(3-chlorophenyl)-1-methyl-2(1H)-quinolinone;

6-[(4-chlorophenyl)hydroxy(1-methyl-1H-imidazol-5-yl)methyl]-4-(3-ethoxyphenyl)-1-methyl-2(1H)-quinolinone;

6-[(4-chlorophenyl)(1-methyl-1H-imidazol-5-yl)methyl]-4-(3-ethoxyphenyl)-1-methyl-2(1H)-quinolinone monohydrochloride monohydrate;

6-[amino(4-chlorophenyl)(1-methyl-1H-imidazol-5-yl)methyl]-4-(3-ethoxyphenyl)-1-methyl-2(1H)-quinolinone, and 6-amino(4-chlorophenyl)(1-methyl-1H-imidazol-5-yl)methyl]-1-methyl-4-(3-propylphenyl)-2(1H)-quinolinone; a stereoisomeric form thereof or a pharmaceutically acceptable acid or base addition salts thereof.

8. The method of claim 1 wherein the compound is (+)-(R)-6-[amino(4-chlorophenyl)(1-methyl-1H-imidazol-5-yl)methyl]-4-(3-chlorophenyl)-1-methyl-2(1H)-quinolinone; or a pharmaceutically acceptable acid addition salt thereof.

9. The method of claim 1 wherein a radiation sensitizing amount of the farnesyl protein transferase inhibitor is administered orally, parenterally, rectally or topically.

10. The method of claim 8 a pharmaceutical composition comprising the compound is administered orally in an amount of from 10 to 1500 mg/m² of the compound, either as a single dose or subdivided into more than one dose.

11. The method of claim 1 wherein the irradiation is ionizing irradiation.

12. The method of claim 1 wherein the irradiation of the tumor is external or internal.

13. The method of claim 1 wherein the effective amount of the farnesyl protein transferase inhibitor is part of a pharmaceutical composition comprising at least the farnesyl protein transferase inhibitor.

14. The method of claim 13 wherein the administration of the pharmaceutical composition commences up to one month before the irradiation of the tumor.

15. The method of claim 1 wherein the irradiation of the tumor is fractionated and the administration of the pharmaceutical composition is maintained in the interval between the first and the last irradiation session.

\* \* \* \* \*